United States Patent [19]
Yoneda et al.

[11] Patent Number: 5,115,403
[45] Date of Patent: May 19, 1992

[54] WORKPIECE WORKABILITY DETECTION METHOD AND A METHOD FOR CUTTING A WORKPIECE BY MEANS OF A CUTTING MACHINE UTILIZING THAT METHOD

[75] Inventors: Akiyoshi Yoneda, Akashi; Mitsuyoshi Sawamura, Kobe; Kikuo Tanaka, Ono; Takashi Kokado, Kasai, all of Japan

[73] Assignee: Amada Company, Limited, Japan

[21] Appl. No.: 305,759

[22] Filed: Feb. 3, 1989

[30] Foreign Application Priority Data

Feb. 4, 1988 [JP] Japan .................................. 63-22878
Mar. 30, 1988 [JP] Japan .................................. 63-74753
Mar. 30, 1988 [JP] Japan .................................. 63-74754
Apr. 4, 1988 [JP] Japan .................................. 63-81186

[51] Int. Cl.⁵ ...................... G06F 15/46; B23D 45/00
[52] U.S. Cl. ........................ 364/474.15; 364/474.17; 364/551.02; 83/72; 73/104
[58] Field of Search ............ 364/474-474.37, 364/551.02, 506, 507; 73/862.06, 862.68, 104; 318/571, 565, 569; 340/825.23, 680, 679, 665; 408/8, 10, 11, 12, 13; 409/80; 83/801, 72, 73, 74, 75, 75.5

[56] References Cited

U.S. PATENT DOCUMENTS

| | | | |
|---|---|---|---|
| 4,031,368 | 6/1977 | Colding et al. | 364/474.17 |
| 4,176,396 | 11/1979 | Howatt | 364/474.17 |
| 4,208,718 | 6/1980 | Chung | 364/474.17 |
| 4,358,974 | 11/1987 | Sakurai | 364/474.17 |
| 4,509,126 | 4/1985 | Olig et al. | 364/474.17 |
| 4,536,849 | 8/1985 | Borisch et al. | 364/474.16 |
| 4,546,910 | 1/1986 | Smith et al. | 364/474.17 |
| 4,547,847 | 10/1985 | Olig et al. | 364/474.15 |
| 4,736,625 | 5/1988 | Patterson et al. | 364/474.17 |
| 4,809,200 | 2/1989 | Moore et al. | 364/474.17 |
| 4,833,617 | 5/1989 | Wang | 364/474.17 |
| 4,855,925 | 8/1989 | Bhateja | 364/474.15 |
| 4,866,429 | 9/1989 | Granere | 364/474.17 |

FOREIGN PATENT DOCUMENTS

1510299 6/1975 United Kingdom .
1504310 10/1975 United Kingdom .
2168828 7/1983 United Kingdom .

*Primary Examiner*—Jerry Smith
*Assistant Examiner*—Jim Trammell
*Attorney, Agent, or Firm*—Wigman & Cohen

[57] ABSTRACT

A workability detection method for a workpiece consisting of the steps of cutting a workpiece, based on specified cutting conditions, detecting the cutting resistance during the cutting operation, or the cutting time or the amount of tool wear to make a cut up to a specified position of the workpiece, or the feeding position of the cutting tool on a workpiece or the amount of processing of the cutting tool after a specified cutting time and comparing the detected data with corresponding data which is stored in a data base.

18 Claims, 8 Drawing Sheets

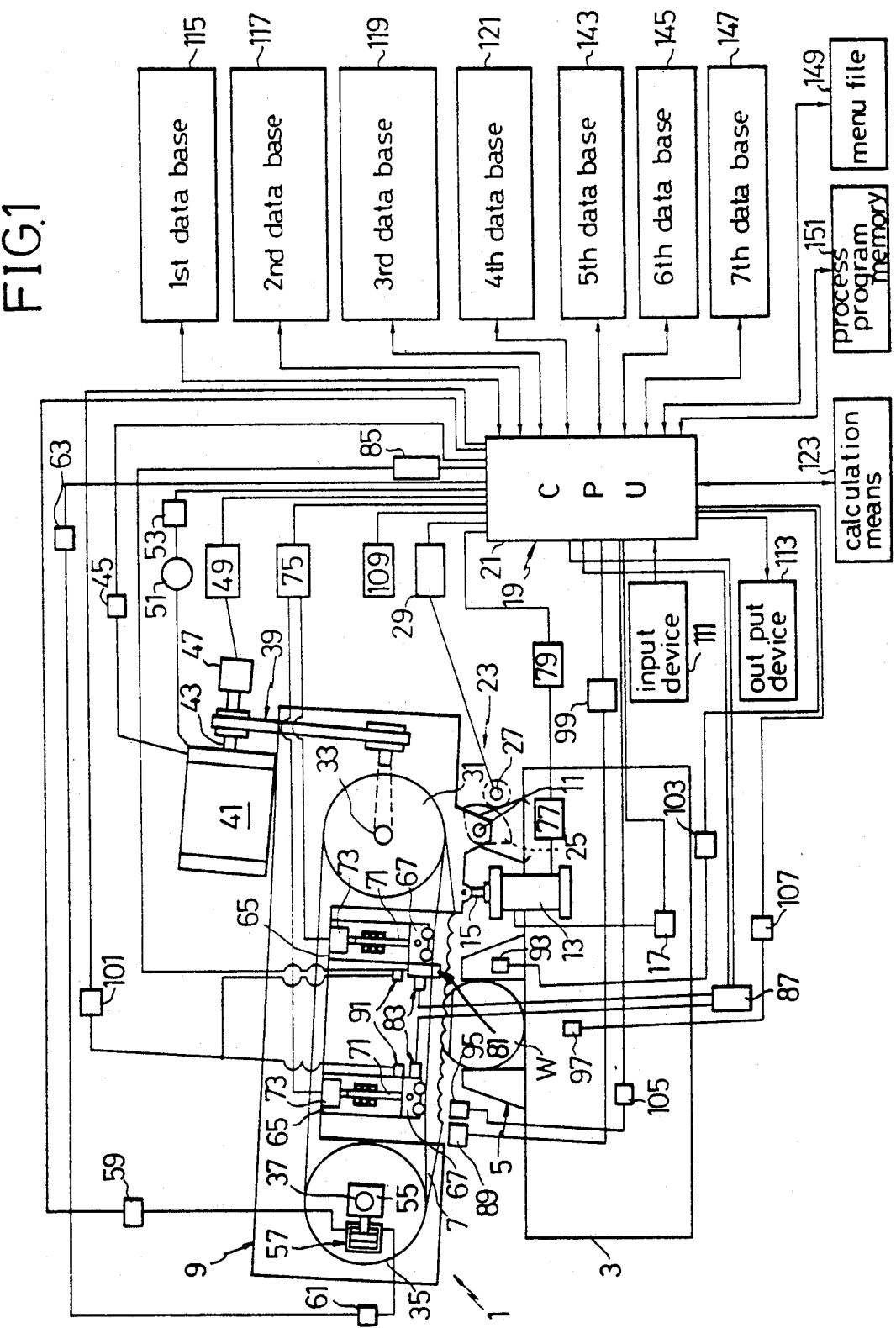

FIG.4

| rearward component force (kg) | | cutting condition |
|---|---|---|
| A 1 | less then 21 | J 4 |
| A 2 | 21~30 | J 5 |
| A 3 | 31~40 | J 1 |

FIG.5

| rearward component force (kg) | | cutting condition |
|---|---|---|
| B 1 | 31~40 | J 6 |
| B 2 | 41~60 | J 5 |
| B 3 | 51~60 | J 7 |

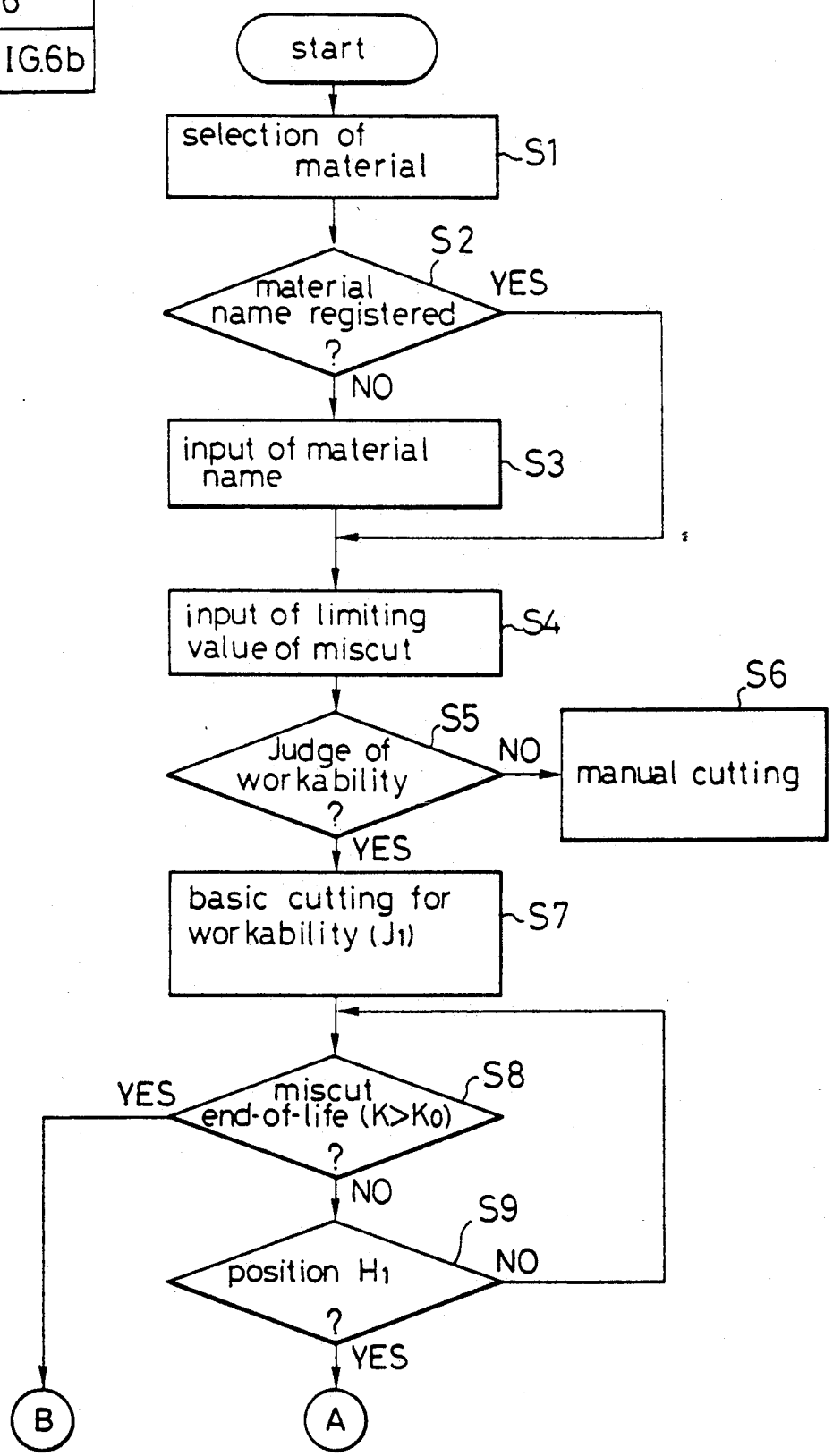

FIG 6.b
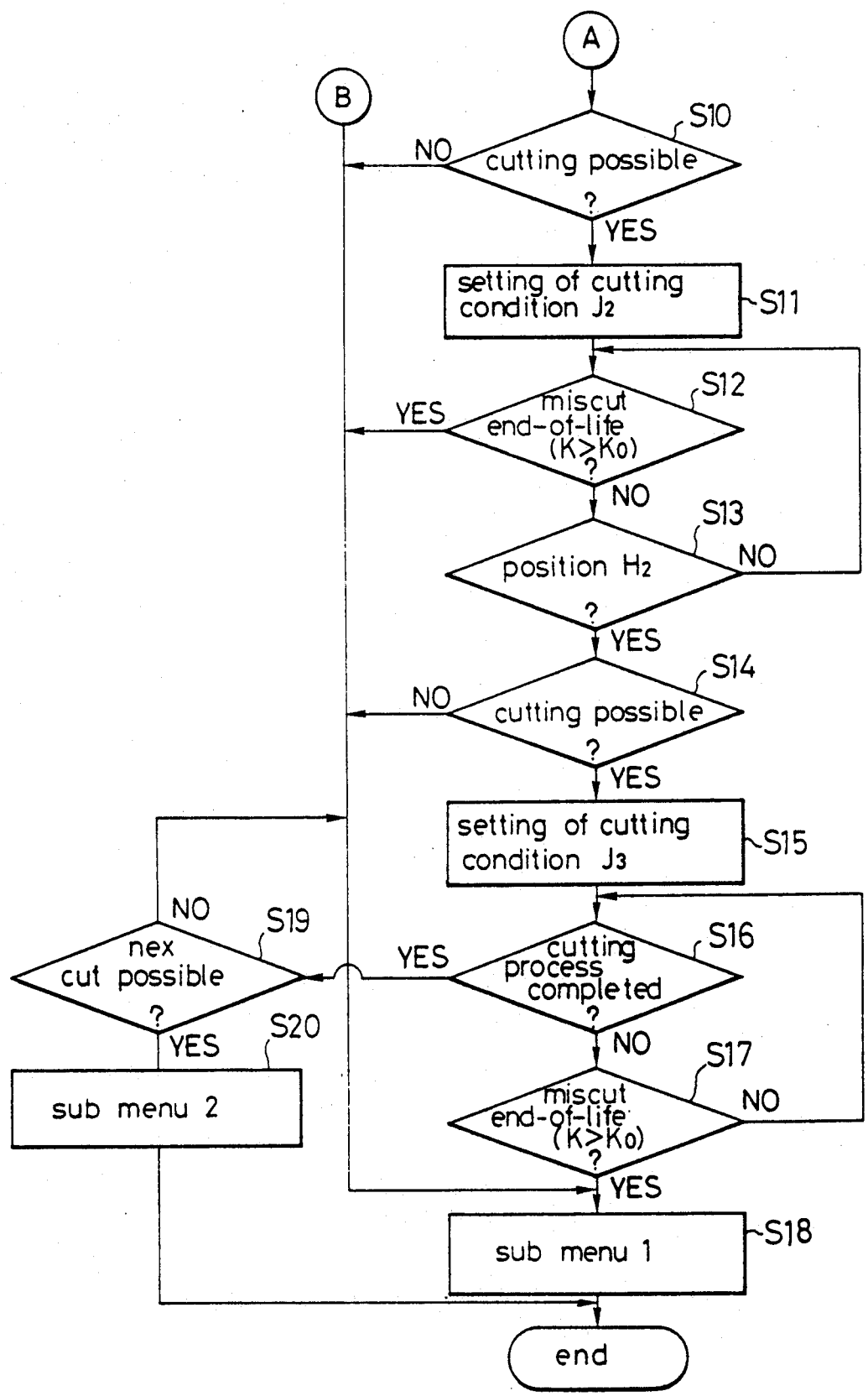

WORKPIECE WORKABILITY DETECTION METHOD AND A METHOD FOR CUTTING A WORKPIECE BY MEANS OF A CUTTING MACHINE UTILIZING THAT METHOD

BACKGROUND OF THE INVENTION

1. Field of the Invention

The present invention relates to a method for detecting the workability of a workpiece in a cutting machine such as, for example, a lathe or sawing machine for cutting a workpiece, and a method for cutting a workpiece by means of a cutting machine.

2. Description of the Prior Art

Conventionally, when beginning to cut a workpiece in a cutting machine such as, for example, a lathe or sawing machine for cutting a workpiece, the workability of the workpiece is not estimated in advance. Specifically, it is normal in a conventional process for the operator, utilizing accumulated experience and intuition, to prepare a cutting manual, and based on that cutting manual, to set the cutting conditions for the workpiece, such as running speed and feeding speed of the cutting tool relative the workpiece, then carry out the cutting process.

In such a conventional process, when the cutting of the workpiece is performed by means of a cutting machine, the workability of each workpiece is not detected. In addition, the detection of the cutting status of the cutting machine is also not carried out. Accordingly, in such a conventional process, it is very difficult to quickly set the appropriate cutting conditions for each workpiece, and it is also extremely difficult to change the cutting conditions to suitably correspond to changes in cutting status during the cutting process.

Specifically, even for workpieces of an identical material there are partial variations in composition and hardness, and there are cases where, strictly, the workability changes in part. In addition, for the workpiece to be cut by sawing machine, surface conditions occur such as black surface and lathe turning surface and the like, so that changes in workability are encountered; i.e., the black surface is harder than inner portion of the workpiece and the lathe turning surfaces show variations in hardness because of differences in the hardening process. In addition, there are cases where the material of the workpiece is unknown and where the workability is unknown for a new material. In cases of this type, it is necessary that the cutting conditions are observed while the workpiece is actually being cut and it is necessary to modify the cutting conditions in a suitable manner.

Accordingly, in determining suitable cutting conditions for the workpiece, it is necessary to make tests cuts on the workpiece with the cutting machine, which requires considerable time and labor and waste of the workpiece. Also, if the cutting conditions are inappropriate when the workpiece is being cut, the process is carried out inefficiently, and on occasion damage to the cutting tool occurs.

SUMMARY OF THE INVENTION

A first object of the present invention is to provide, with due consideration to the drawbacks of such conventional method, a detection method for detecting the workability of a workpiece by carrying out a cutting process under suitable cutting conditions.

A second object of the present invention is to provide a cutting method by which suitable cutting conditions are evaluated at a suitable number of locations during the course of the cutting process, and cutting is performed under the suitable cutting conditions, when the cutting process is being performed on the workpiece.

These objects are achieved in the present invention by the provision of various types of sensors on the cutting machine, wherein the data detected by the sensors are compared with data stored in a data base.

BRIEF DESCRIPTION OF THE DRAWINGS

These and other objects, features, and advantages of the present invention will become more apparent from the following description of the preferred embodiments taken in conjunction with the accompanying drawings, in which:

FIG. 1 is an explanatory drawing for an embodiment of a cutting machine and a control system thereof, according to the present invention.

FIG. 4 and FIG. 5 are explanatory drawings showing an example of the data for the cutting conditions and the rearward component force of the cutting resistance, stored in a second and a third data base.

FIGS. 6a and 6b are flowcharts showing one example of the cutting method.

DETAILED DESCRIPTION OF THE PREFERRED EMBODIMENTS

Figure 3B:
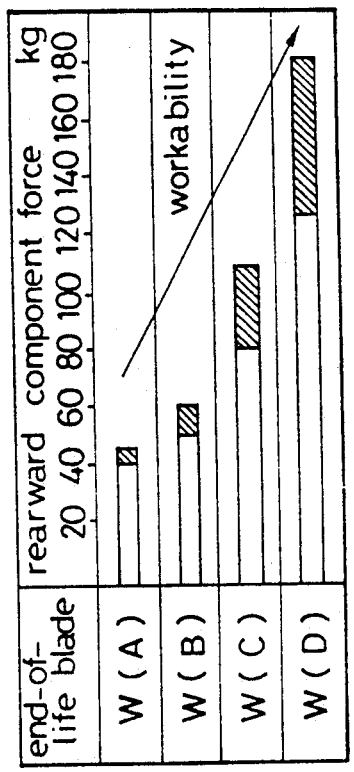
FIGS. 3a and 3b are is explanatory drawings showing the relationship between the kind of the workpiece and the rearward component force of the cutting resistance, stored in a first data base.

Now referring to FIG. 1, although a horizontal bandsaw 1 is used as an example of a preferred embodiment of the cutting machine of the present invention, an upright bandsaw or a circular saw could just as easily be used as the sawing machine.

Because the general configuration of the horizontal band saw 1 is already well known, the cutting machine 1 is shown in schematic form only in FIG. 1 and an explanation is given with respect to the outline configuration related to the embodiment of the present invention.

The bandsaw machine 1 is mounted on a base 3, and a vise device 5 is installed for freely clamping and securing a workpiece W. A cutting head 9 equipped with a sawblade 7 as a cutting tool is provided with full freedom of movement in the vertical direction.

As a result of this configuration, the cutting head 9 in this embodiment of the present invention is supported in a freely rotating manner in the vertical direction through a hinge pin 11.

In order to move the cutting head 9 in the vertical direction, a piston rod 15 of an elevating hydraulic cylinder 13 mounted on the base 3 is connected in a pivotally supporting manner to the cutting head 9. Accordingly, the cutting head 9 is elevated by supplying oil under pressure to the elevating hydraulic cylinder 13, and is caused to descend by discharging the pressurized oil from the elevating hydraulic cylinder 13. At this time, a flow control valve (omitted from the drawings) in a hydraulic circuit (also omitted from the drawings) is suitably controlled. By controlling the amount of pressurized oil discharged from the elevating hydraulic cylinder 13, the speed of descent of the cutting head 9, and therefore the speed at which the sawblade 7 cuts into the workpiece W, can be controlled.

A feeding control device 17 is linked to the elevating hydraulic cylinder 13 to control the speed of cutting into the workpiece W in the above-described manner. The feeding control device 17 is connected to a central processing unit (CPU) 21 in a control device 19. The flow control valve is controlled based on data input from the CPU 21 to control the speed at which the sawblade cuts into the workpiece W.

A feeding position detection device 23 is provided to detect the position of the cut of the sawblade 7 into the workpiece W. Specifically, in this embodiment of the present invention, a sector gear 25 is mounted on the hinge pin 11, and the gear of a rotary encoder 27 engages the sector gear 25. The rotary encoder 27 is connected to the CPU 21 through a interface 29.

Accordingly, because the rotary encoder 27 is rotated through the linkage to the vertical movement of the cutting head 9, the number of pulses output from the rotary encoder 27 is counted, and the vertical position of the cutting head 9, that is, the depth of cut of the sawblade 7 into the workpiece W, can be accurately detected by suitable calculations.

In the cutting head 9, a drive wheel 31 which turns the sawblade 7 is supported in a freely rotatable manner through a driveshaft 33, and a follower wheel 35 is supported in a freely rotatable manner through a follower shaft 37. Accordingly, the sawblade 7 can be driven by suitable operation of the drive wheel 31, and, as previously outlined, the cutting head 9 is caused to descend and the sawblade 7 to cut into the workpiece W so that the cutting of the workpiece W is carried out.

In order to rotatingly drive the drive wheel 31, the driveshaft 33 is connected to an output shaft 43 of a servomotor 41 through a power transmission mechanism 39, such as a belt power transmission mechanism. In order to control the rotation of the servomotor 41 and thus control the running speed (speed of cutting) of the sawblade 7, a rotation control device 45 is connected to the servomotor 41. The rotation control device 45 is connected to the CPU 21 and the rotation of the servomotor 41 is controlled according to the control data input from the CPU 21.

A rotation sensor 47 is provided on the output shaft 43 of the servomotor 41 to detect the main component force of the cutting resistance (the cutting resistance in the running direction of the sawblade 7) when the workpiece W is being cut by the sawblade 7. The rotation sensor 47 is connected to the CPU 21 through the interface 24.

Accordingly, when the workpiece W is being cut by the sawblade 7, the RPM of the servomotor 41 changes according to the change in cutting resistance, whereupon this change in RPM is detected by the rotation sensor 47. Then, a signal corresponding to the main component force of the cutting resistance is output from the rotation sensor 47 and input to the CPU 21 through the interface 49, so that the main component force of the cutting resistance is detected through a suitable calculation process.

In detecting the main component force of the cutting resistance, in place of the rotation sensor 47, a detection device 51, such as an ammeter, wattmeter, or torque detector may be suitably connected to the servomotor 41, and the detection device 51 can be connected to the CPU 21 through the interface 53.

The follower shaft 37 of the follower wheel 35 is supported on a sliding base 55 which can be moved toward or away from the drive wheel 31. The sliding base 55 is connected to a hydraulic cylinder 57 mounted on the cutting head 9. Accordingly, the operating fluid is supplied to the hydraulic cylinder 57 by the energization which forces the follower wheel 35 away from the drive wheel 31, and can impart suitable tension to the sawblade 7.

In order to control the tension on the sawblade 7, a tension control device 59 is connected to the hydraulic cylinder 57, and the tension control device 59 is connected to the CPU 21. The tension control device 59 controls the pressure of the operating fluid fed to the hydraulic cylinder 57, based on the output data from the CPU 21, and controls the tension of the sawblade 7 in this manner.

In addition, a tension sensor 61 is connected to the hydraulic cylinder 57, and the tension sensor 61 is connected to the CPU 21 through the interface 63. The tension sensor 61 may be, for example, a hydraulic sensor or the like, which can detect the tension in the sawblade 7 by detecting the pressure in the hydraulic cylinder 57. Accordingly, the tension in the sawblade 7 can be controlled to a suitable tension, and breakage of the sawblade 7 caused by overtension, or a miscut in the workpiece W from insufficient tension of the sawblade 7 can be prevented.

Further, in the sawing machine 1, a sawblade guide 65 is provided in the cutting region where the sawblade 7 cuts the workpiece W, to guide the sawblade 7 so that the teeth thereof directs in the downward perpendicular direction.

A side surface guide (omitted from the drawings) for interposedly supporting and guiding the sawblade 7 is provided on the sawblade guide 65, and a rear surface restraining member 67 provided with a roller for guiding and supporting the rear surface of the sawblade 7 is provided so that it can move vertically. The rear surface restraining member 67 touches the rear surface of the sawblade 7. An elevating rod 71 is linked to the upper surface of the rear surface restraining member 67. A rear component force detection sensor 73, such as a pressure element, a load cell, or the like, is provided on the upper edge of the elevating rod 71. The rear component force detection sensor 73 is connected to the CPU 21 through an interface 75.

Accordingly, to cut the workpiece W, the cutting head 9 is caused to descend, whereupon the cutting of the workpiece W is performed by the sawblade 7 and the rearward component force of the cutting resistance can be detected by the rear component force detection sensor 73.

Further, a pressure gauge 77 is connected to the elevating cylinder 13 and this pressure gauge 77 is connected to the CPU 21 through an interface 79. The rearward component force of the cutting resistance can be detected as a result of this configuration.

A miscut detection device 81 and a bending sensor 83 are provided on the sawblade guide 65. The miscut detection device 81 and the bending sensor 83 are connected to the CPU 21 through an interface 85 and an interface 87 respectively.

When the workpiece W is cut the miscut detection device 81 detects any deflection in the rear-front direction of the sawblade 7 (the direction perpendicular to the sheet in FIG. 1), for detection of miscuts. The bending sensor 83 detects any distortion on the rear surface side of the sawblade 7 so that the rearward component force of the cutting resistance can also be detected by the use of the bending sensor 83.

Further, a tool wear measurement device 89, a surface roughness measurement device 91, a vibration sensor 93, a noise sensor 95, and a non-contact type temperature sensor 97 are provided in the sawing machine 1 to detect the cutting status of the workpiece W by the sawblade 7. These devices are connected to the CPU 21 through a plurality of interfaces 99, 101, 103, 105, and 107 respectively.

A CCD camera, for example, can be used as the tool wear measurement device 89. In this case, the shape of the teeth of a new sawblade 7 is photographed before use, then on the next occasion, after use, the shape is again photographed and compared with the original photograph. In this way the wear of the teeth can be measured. When the teeth of the sawblade 7 are photographed with a CCD camera the operation of the sawblade must be stopped. If a high speed camera is used it is possible to photograph the shape of the sawblade teeth during operation.

The surface roughness measurement device 91 contacts the cut surface of the workpiece W directly and measures the surface roughness. After the workpiece W is cut and the cut-out section removed, the surface roughness measurement device 91 is lowered from , for example, the cutting head 9 to a position on the cut surface of the workpiece W. Any measuring element which can freely contact the cut surface of the workpiece is acceptable as the surface roughness measurement device 91. For example, it is possible to use a differential transformer. In addition, by tracing the cut surface of the workpiece W using the surface roughness measurement device 91, the amount of the cut can be detected.

The vibration sensor 93 can be any device which detects the vibration of the sawblade 7 when the workpiece W is being cut. Any suitable vibration meter can be used, but it is preferable that the position of such a device be the position of the vise device 5 close to where the sawblade 7 cuts the workpiece.

The noise sensor 95 should be a device which detects a change of noise at the cutting section when the workpiece W is being cut by the sawblade 7. However, a microphone with directivity capabilities is preferable.

As the non-contact type temperature sensor 97, an infrared sensor, for example, which can detect the temperature of the section of the workpiece being cut, when cutting a workpiece of several millimeters in thickness without using cutting oil, is desirable.

As outlined above, in cutting the workpiece W with the sawing machine 1, it is important to determine the workability of the workpiece W to cut that workpiece with good efficiency. Specifically, if the cutting is commenced with high speed for the workpiece made of difficult-to-cut material such as titanium alloy or the like, the teeth of the saw blade may be broken during the operation. Accordingly, a method for determining the workability of the workpiece W will now be explained.

Figure 2:
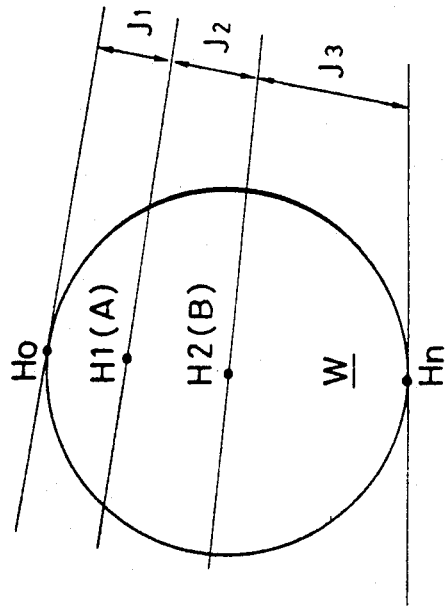
FIG. 2 is an explanatory drawing, explaining the method of detecting the workability of the workpiece and the method of cutting the workpiece.

In determining the workability of the workpiece W, as shown in FIG. 2, a cut is performed from an initial position Ho on the workpiece W to a specified position H1 under specified cutting conditions J1. The specified cutting conditions J1, is preferably such that a speed of movement of the sawblade 7 (running speed) is slower than the saw velocity when normal sawing occurs and cutting area per unit time interval (cutting efficiency) is smaller than normal cutting efficiency, so that the load which acts on the sawblade 7 is relatively small.

The abovementioned specified cutting condition J1 is achieved by controlling the servomotor 41 under the control of the rotation control device 45 to rotate at a relatively low speed, and the cutting head 9 under the control of the feeding control device 17 to descent at a comparatively low speed.

In cutting the workpiece W under specified cutting conditions such as the abovementioned J1, the cutting head 9 descends from the maximum elevation and, when the sawblade 7 reaches the initial position H0, the speed of the saw and the rate of descent of the cutting head are controlled under the specified conditions J1. Whether the sawblade 7 reach the initial position H0 is detected by the feeding position detection device 23. Because the load which acts on the sawblade 7 changes considerable when the sawblade 7 touches the workpiece W, it is also possible to detect the initial position H0 by detecting the load change using the detecting device 51.

While the sawblade 7 is descending from the initial position H0 to the specified position H1, the rearward component force of the cutting resistance is detected by means of the rearward force component detection sensor 73 and the main component force of the cutting resistance is detected by means of the rotation sensor 47, the detection device 51 or the like. In this way, the cutting resistance on the workpiece W can be determined by detection of the rearward component force and the main component force of the cutting resistance, and the workability of the workpiece W with respect to the sawblade used can be determined.

The rearward component force and the main component force detected for the cutting resistance may be the momentary rearward component force and main component forces when the sawblade reaches the prescribed position H1, or the integrated or average value of the rearward component force and main component force from the initial cutting position H0 to the prescribed position H1.

In addition, the workability of the workpiece can be detected by measuring the wear on the teeth of the sawblade 7 using the tool wear measurement device 89 when the specified position H1 is reached under the specified cutting conditions J1, instead of by detection of the rearward component force and main component forces of the cutting resistance.

Also, the workability of the workpiece W can be detected by timing the elapsed cutting time from the initial position H0 on the workpiece W to the specified position H1 under the specified cutting conditions J1, using a clock 109 (as shown in FIG. 1) connected to the CPU 21. Further, instead of measuring the elapsed cutting time as outlined above, the moment-by-moment feeding speed of the saw blade 7 with respect to the workpiece W can be detected from time to time, and the workability of the W can also be determined by detecting the average feeding speed from the initial position H0 on the workpiece W to the specified position H1.

Furthermore, in the case where the cutting is commenced from the initial position Ho under the specified cutting conditions J1, after a fixed period of time has elapsed, it is possitlbe to determine the workability of the workpiece W by detecting the amount of processing (amount of work) done by the sawblade 7, or by detecting the feeding position of the sawblade 7 with respect to the workpiece W.

In addition, in the case where one of the cutting conditions, for example, the running speed of sawblade or the feeding speed of cutting head being maintained constant and the other cutting condition is controlled so that the cutting resistance has a specified value, by detecting the latter cutting conditions (i.e. running speed or feeding speed of sawblade), the workability of the workpiece W can be determined.

Now, as shown in FIG. 1, an input device 111, such as a keyboard, is provided for input of the type of material and the shape of the workpiece W to the CPU 21, and an output device 113 such as a CRT or the like is hooked up for displaying data such as the measured rearward component force, main component force, and the like. In addition, a first data base 115, a second data base 117, a third data base 119, and a fourth data base 121, and a calculation means 123 are connected to the CPU 21.

In the first data base 115, data corresponding to the rearward and main component forces of the cutting resistance measured when the workpiece W is cut under the specified cutting conditions J1, as well as the cutting time, the feeding position, the amount of wear on teeth and the like are stored in advance as back-up data for each element such as the type of the sawblade 7, the material, shape, dimensions, hardness, and the like of the workpiece W and the like. In addition, newly measured data for the rearward and main component forces of the workpiece, the cutting time, the feeding position, the amount of wear on teeth and the like are also stored in the first data base 115 as back-up data.

Accordingly, when the workpiece W is cut, the cutting of the workpiece under the specified cutting conditions is initiated, and one item from among the rearward component force, the main component force, the cutting time, the feeding position, the amount of wear on the teeth, and the like is measured. Then, by retrieval of the data from among the rearward component force, the main component force, the cutting time, the feeding position, the amount of wear on the teeth, or the like, stored in advance in the first data base 115 as back-up data, it is possible to compare the measured data with the stored data to determine the workability of the workpiece W. In this case, even in the event that there is considerable variation in the texture and hardness of the workpiece, or if the workpiece is a new type of steel the quality of which is unknown, it is still possible to distinguish the workability.

A more detailed explanation will now be given. In the first data base 115, as indicated in FIGS. 3a and 3b for example, the rearward component forces when each workpiece of a plurality of workpieces W(A), W(B), W(C), and W(D) is cut by a new sawblade and an end-of-life sawblade (i.e. a sawblade at its end of life) under the specified cutting conditions J1 are stored as back-up data in the form of a graph.

Figure 3A:
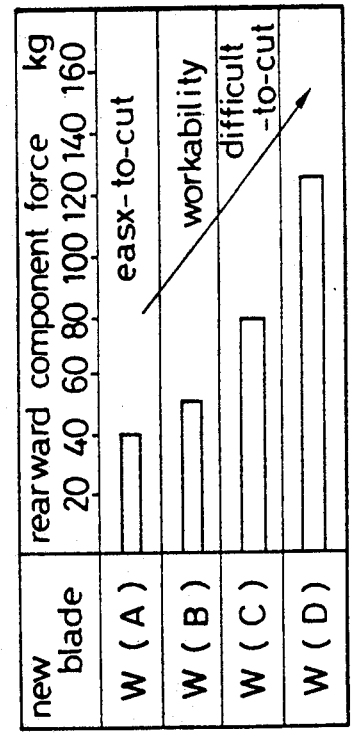

Accordingly, when the workpiece W is cut to the specified position H1, based on the specified cutting conditions J1, if the saw blade 7 is new and if the rearward component force is detected to be, for example, 50 kg, the rearward component force data shown in FIG. 3a stored in the first data base 115 is extracted and, by comparison in the calculation means 123, it can be determined that the workability of the workpiece W corresponds to that of the workpiece W(B). On the other hand, in the case where the sawblade 7 has been used and the teeth are worn and the workpiece W(B) is being cut, the cutting resistance of the workpiece W is compared with that of workpiece W(B) shown in FIG. 3b, and it is determined whether the life of the sawblade 7 has been terminated or not. Further, referring to FIG. 3b, it is found that although the sawing of the workpiece W(B) is difficult and the sawing of the workpiece W(A) is possible; accordingly, the sawblade 7 can be effectively utilized. In addition, by making a comparison with the data on the life of sawblades, the life expectancy of the sawblade 7 can be determined.

Now, data related to the previously set the cutting conditions J4, J5, J1 and the rearward component forces A1, A2, and A3 are stored in the second data base 117, as shown in FIG. 4, in order to determine the cutting conditions J2 when the workpiece W is subjected to the sawing process at the specified position H1 shown in FIG. 2.

Also, data for to the cutting conditions J6, J5, J7 and the rearward component force B1, B2, and B3 are stored in the third data base 119, as shown in FIG. 5, in order to determine the cutting conditions J3 when the workpiece W is subjected to the sawing process at the specified position H2 shown in FIG. 2

Data relating to the relation between the dimensions and shape of each of many workpieces W and the limiting value of the amount of miscut for each kind of sawblade are stored in the fourth data base 121.

Accordingly, after the cutting of the workpiece W under the specified cutting conditions J1 is performed as previously outlined, the workability of the workpiece W at the specified position H1 is determined, and the conditions J2 for cutting from feeding position H1 to the next feeding position H2 are determined. Further, after determining the conditions J3 for cutting to the next feeding position Hn, the cutting process on the workpiece W from the feeding position H2 to feeding position Hn is performed, and the workpiece W can be sawn at good efficiency without placing an added burden on the sawblade 7.

An explanation will now be given based on the flowchart of FIG. 6 for the sawing process on the workpiece W whereby the cutting conditions for the workpiece W are consecutively determined.

In FIG. 6, in step S the quality, dimensions, shape, and the like which define the material name for the workpiece W are selected. In step S2 it is determined whether or not the material name is already registered. If the material name has not yet been registered, in step S3 the material name is input by means of the input device 111 and the program proceeds to step S4. If in step S2 the material name has already been registered, the program proceeds directly to step S4.

In step S4, the limiting value Ko of the miscut in the workpiece W is input from the input device 111 and is filed in the fourth data base 121.

In step S5 a selection is made as to whether or not the workability of the workpiece W is determined. If it is decided that the workability of the workpiece W is not determined, in step S6 the workpiece is cut manually. If the selection is made to determine the workability of the workpiece, in step S7 the basic cutting for determining the workability, specifically, the cutting process at the specified cutting conditions J1, is initiated.

After the cutting process is initiated, in the interval to reach the feeding position H1, the determination is made in step S8 whether or not the life of the sawblade for cutting the workpiece is ended, by the magnitude of miscut K. Specifically, the actual amount of miscut K detected by the miscut detection device 81 is introduced into the CPU 21. Miscut limiting value data Ko filed in the fourth data base 121 is introduced into the CPU 21, and both the actual amount of miscut K and the miscut limiting value data Ko are compared in the calculation means 123. If the actual amount K of miscut is greater than the miscut limiting value Ko, the life of sawblade for cutting the workpiece being ended, is determined (the situation is called that the sawblade reaches "miscut end-of-life") and the program proceeds to step S18. From the submenu 1 of step S18, material change, or sawblade change, or both material and sawblade change are selected, and the program ends.

If the actual amount of miscut is within the miscut limiting value it is determined that the life of the sawblade for cutting the workpiece is not ended, and in step S9 the decision is made whether or not the feeding position is the position H1 for determining the next cutting condition. If not the position H1, the program returns to the step S8.

If the decision is made that it is the position H1, a judgment is made in step 10 as to whether cutting is possible or not by an appropriate cutting condition. Specifically, the rearward component force of the cutting resistance at the discriminant position H1 is detected by the rearward component force detection sensor 73. The actual rearward component force detected (A) is introduced into the calculation means 123 connected to the CPU 21. Then data related to the previously set cutting conditions J4, J5, J1, and the rearward component forces A1, A2, and A3 at position H1, filed in the second data base 117 as shown in FIG. 4, is introduced to the calculation means 123. In the calculation means 123, the actual rearward component force (A) is compared with the rearward component forces A1, A2, and A3 which are stored in the data base 117 together with corresponding cutting conditions J4, J5, J1. Specifically, if the current rearward component force (A) exceeds 40 kg, the cutting process is impossible because no cutting condition, corresponds to the rearward force component A larger than 40 Kg, and the program proceeds to step S18. From the submenu 1 of step S18, material change, or sawblade change, or both material and sawblade change are selected, and the program ends.

If the actual rearward component force (A) is in the 31 to 40 kg range, the decision is made to carry out the cutting under the cutting condition J1; if the force (A) is in the 21 to 30 kg range the decision is made to carry out the cutting under the cutting conditions J5; and if the force (A) is less than 21 kg, the decision is made to carry out the cutting under the cutting conditions J4.

Accordingly, if the actual detected rearward component force (A) is, for example, 25 kg, then it is judged that cutting is possible, and the cutting conditions J2 from positions H1 to position H2 are set to the cutting conditions J5 of the data base in step S11.

Under the cutting conditions J5, the cutting process is continued, and in the interval up to the discriminant position H2, the judgment about the miscut end of life is made in step S12, in the same way as when a judgment is If the judgment is made that there is the "miscut end-of-life", the program proceeds to step 18 to perform the same processing as described before. If the judgment negative, the decision is made at step S13 as to whether or not the position is the feeding position H2 for determining the third cutting condition J3, and if it is not the position H2 the program returns to the step S12.

If the position is the determinant position H2, the decision is then made at step S14 as to whether cutting is possible from position H2 to position H3 under an appropriate cutting condition. Specifically, at the determinant position H2 the rearward component force is detected by the rearward component force detection device 73 as the cutting resistance. The detected rearward component force detected (B), is introduced into the calculation means 123 connected to the CPU 21. Then data related to the previously set cutting conditions J6, J5, J7 and the rearward component forces B1, B2, and B3 at position H2, filed in the third data base 119, as shown in FIG. 5, is introduced into the calculation means 123. The actual rearward component force (B) is compared with the data related to the previously set cutting conditions J6, J5, J7, and the rearward component forces B1, B2, B3 in the calculation means 123. Specifically, when the current rearward component force (B) exceeds 60 kg, the decision is made that it is not possible to make the cut because no cutting condition corresponds to the rearward force component larger than 60 Kg. The program then proceeds to step S18, and the process previously outlined is performed.

If the actual rearward component force is in the 51 to 60 kg range, it is judged the cutting can be carried out under the conditions J7 in step 15. Also, if the actual rearward component force is in the 41 to 50 kg range, the judgment is made that it is possible to carry out the cutting under the current cutting conditions J5. In addition, if the actual rearward component force is less than 41 kg, the judgment is made that the cutting can be carried out under the conditions J6.

If the actual detected rearward component force (B) is 45 kg, then it is judged that cutting is possible and the cutting conditions J3 are set to the cutting conditions J5 in step S15.

Under the cutting conditions J5 the cutting process is continued, and the judgment is made as to whether the cutting operation is completed, in step S16. If the judgment is made that one cutting is not completed then it is judged at step S17 that there is miscut, end-of-life. If the judgment is made that there is the miscut end-of-life, the program returns to the step S16.

When the judgment is made that the life of the sawblade and/or workpiece is ended the program proceeds to step S18 where a material change, a sawblade change, or both material and sawblade change are selected from the submenu 1. The program then ends.

If the judgment is made in step S16 that one cutting operation is completed, the program then proceeds to step S19 where a judgment is made as to whether or not the next cut is possible. If it is judged that the next cut is not possible the program proceeds to step S18 where the same handling as previously noted takes place. If it is judged that the cut is possible, the program then proceeds to the sub menu 2 of step S20 where it is determined whether cutting under conditions J1, or continuous cutting, or manual cutting will be performed, and a material change, a sawblade change, or both material and sawblade change are selected, or JOB END is selected.

In this way, when the cutting process is performed on the workpiece W, this cutting process is first performed under a suitable process conditions, for example, under the cutting process conditions J1, where the load is smaller than for normal cutting conditions, and, the cutting resistance is detected at a previously set feeding position H1. The actual cutting resistance detected, and for example, the rearward component force, is compared with the cutting resistance data previously-compiled in the second data base 117. The suitable cutting conditions J2 can then be determined, based on the result of this comparison.

Next, cutting is performed at the suitable cutting conditions J2, and the actual cutting resistance, for example, the rearward component force, is detected at a suitable number of positions, for example, at the feeding position H2. Based on the results of the comparison of the actual cutting resistance detected, with the rearward component force of the cutting resistance data previously filed in the third data base 119, the suitable cutting conditions J3 is determined. Therefore, it is possible to automatically determine the cutting conditions during the cutting of each workpiece W, and to set the suitable cutting conditions to cope with that cutting status.

In addition, in the workability detection method and the cutting process method of this embodiment of the present invention, it is possible to detect the main component force instead of the rearward component force as the cutting resistance, and also to detect both the rearward component force and the main component. Also, instead of the cutting resistance, it is possible to detect the cutting time duration, or the amount of wear on the teeth of the sawblade when a cut is made as far as a specified position, or the feeding position or the amount of processing when a specified time cut is made.

As can be readily understood from the above explanation of the embodiment, by means of the present invention, the workability of the workpiece can be easily and reliably detected based on the specified cutting conditions, by means of the cutting resistance, or the cutting time duration, or the amount of wear on the teeth of the sawblade, or the amount of processing, or the feeding position.

In addition, when a cutting process is performed on a workpiece, the cutting process is performed based on the specified cutting conditions. At a previously set feeding position, the cutting resistance, the cutting time duration or the amount of wear on the teeth of the sawblade is detected; or, the amount of processing or the feeding position for a predetermined time duration is detected. The actually detected cutting resistance, or the cutting time duration, or the amount of wear on the teeth, or the amount of processing, or the feeding position is compared with the data for the cutting resistance, or the cutting time duration, or the amount of wear on the teeth, or the amount of processing, or the feeding position previously filed in the data base, and suitable cutting conditions are determined based on this comparison.

Next, the cutting process is continued under the suitable cutting conditions, and actual cutting resistances are further detected at a number of suitable feeding positions. The actually detected cutting resistances are compared with the data for the cutting resistances previously filed in the data base, and based on the results of that comparison, suitable cutting conditions for following cutting steps are determined. Here, again, the suitable cutting conditions can be determined by using data for the cutting time duration or the amount of wear on the teeth, or the amount of processing, or the feeding position, or the like, instead of cutting resistance data. Therefore, it is possible to automatically detect the cutting status during the cutting of each workpiece, and to determine suitable cutting conditions to cope with that cutting status.

Accordingly, it is possible to efficiently cut the workpiece without overloading the sawblade.

The above explanation was given with respect to the horizontal bandsaw 1 as the cutting machine in the embodiment of the present invention. However, it is possible to implement the method of detecting the workability of the workpiece W for many types of machine tools which perform a cutting process on the workpiece W.

Figure 7:
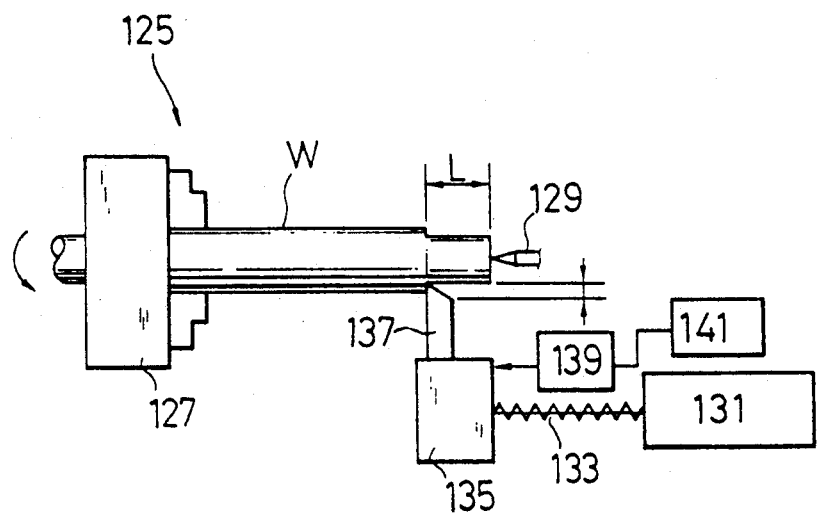
FIG. 7 is an explanatory drawing showing an outline of an embodiment of the present invention in the case of evaluating the workability of a workpiece in a lathe.

For example, in the case where a lathe is used as an example, as shown schematically in FIG. 7, one end of the workpiece W is clamped in a freely rotatable chuck 127 on a lathe 125. The other end of the workpiece is supported, as required, by means of a rotating center 129, and the workpiece W is rotated at a specific RPM. A guide screw 133 is rotated by means of a constant load feeding device 131, and is fed in the lateral direction of a tool post 135. The cutting of the workpiece W is performed by means of a cutting tool 137 mounted on the tool post 135, based on a uniform cutting amount H.

In this case, the RPM of the chuck 127 is a specified rate of rotation, and the cutting amount H is uniform. In addition, the cutting of the workpiece W is carried out under specified conditions for which the load on the cutting tool 137 becomes uniform from the constant load feeding device 131.

Accordingly, the fact that the cutting tool 137 cuts the workpiece W to a uniform length L is detected by a measuring apparatus 139 such as a linear scale or a displacement gauge; and by measuring a cutting time interval which cuts a uniform length L, using a clock 141, the workability of the workpiece W is determined.

Specifically, in the case of this embodiment of the present invention, because data for the cutting time interval, related to each type of dimension, and to the material quality of the workpiece is previously stored in the first data base 115, it is possible to determine the workability of the workpiece W by comparing the back-up data in the first data base 115 with the cutting time interval when the workpiece W is actually cut.

Further, in this embodiment of the present invention, in determining the workability of the workpiece W, as data previously stored in the first data base 115, other than the previously mentioned cutting time interval, suitable data such as the cutting resistance and the feed distance per unit of constant time interval can be used.

Further, in the case where the workpiece W is long, in order to improve the cutting efficiency it is preferable to increase, the feeding speed of the cutting tool 137 during the cutting operation on the workpiece W. In this case, the constant load feeding of the cutting tool 137 by the feeding device (B) is terminated. And in order to change the feeding speed of the cutting tool 137 while performing the cutting process on the workpiece, the cutting resistance or the required cutting time period for performing the predetermined amount of processing is detected. The detected data are compared with corresponding data which are stored in the second data base, related to the cutting conditions. Then, change is made of the feeding speed of cutting tool according to the result of the comparison.

Further, an occasion the cutting resistance or the like at a plurality of feeding positions are detected, to compare the detected data with data which are stored in a plurality of data base related to the cutting condition. Then, change is made of the feeding speed of the cutting tool at a plurality of feeding positions according to the result of the comparison.

Those cutting method in which the feeding speed of the cutting tool 137 is changed at a plurality of feeding position to perform the cutting process on the workpiece is effective in the cutting operation, such as removing black surfaces from the workpiece by the lathe where the high process accuracy is not required. Further, this type of cutting process method can also be applied to cutting machine similar to the lathe.

Again referring to FIG. 1, a fifth data base 143, a sixth data base 145, and a seventh data base 147, as well as a menu file 149 in which is filed a menu containing the material, shape, and dimensions of the workpiece, are connected to the CPU 21. In addition, a process program memory 151 for activating the horizontal bandsaw 1 by entry of the cutting conditions from the input device 111 is connected to the CPU 21.

Figure 8:
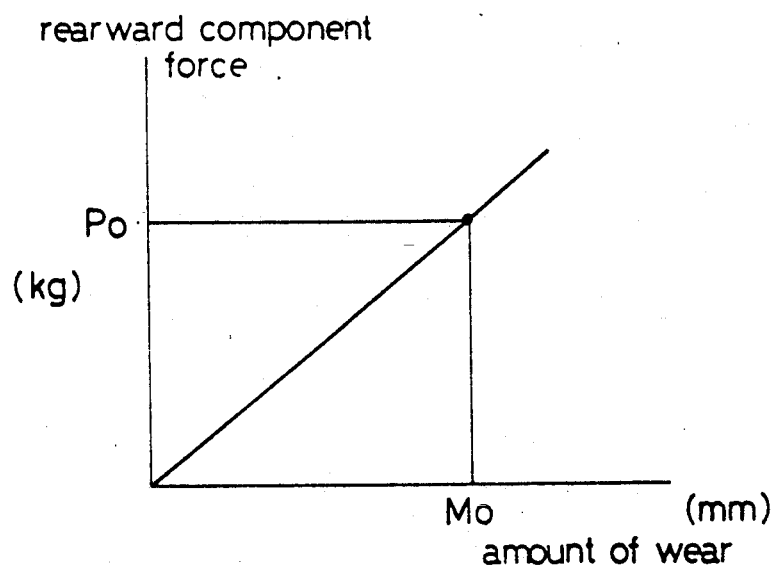
FIG. 8 is an explanatory drawing showing data for the relationship between the amount of wear on the teeth of a sawblade and the rearward component force of the cutting resistance, stored in a fifth data base.

As shown in FIG. 8, for each material, dimensions, shape of the workpiece, or cutting conditions, data for the rearward component force related to amount of wear on the sawblade 7, are filed in the fifth data base 143 as a data base. In FIG. 8, the amount of wear Mo corresponding to the rearward component force Po is the limiting value of the wear. Thus by comparing the actual detected back pressure component P with the previously set Po, a determination of whether the sawblade 7 is being within its life or not can be made.

Figure 9:
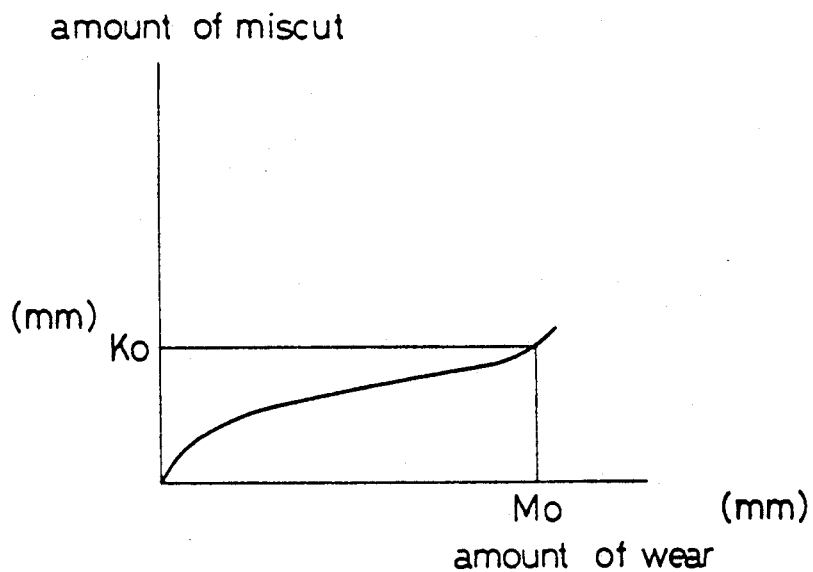
FIG. 9 is an explanatory drawing showing data stored in a sixth data base, giving the relationship between the amount of wear on the teeth of a sawblade and the amount of miscut in the cut.

As shown in FIG. 9, for each material, dimensions, shape of the workpiece W, or cutting conditions, data for the amount of miscut related to amount of wear on the sawblade 7, are filed in the sixth data base 145 as a data base. In FIG. 9, the amount of wear Mo corresponding to the amount of miscut Ko is the limiting value of the wear. Thus by comparing the actual detected miscut amount K and the previously set Ko, a determination of whether the sawblade 7 is being within its life or not, can be made. Further, in this case, obviously, the amount of miscut can also be forecast.

Figure 10:
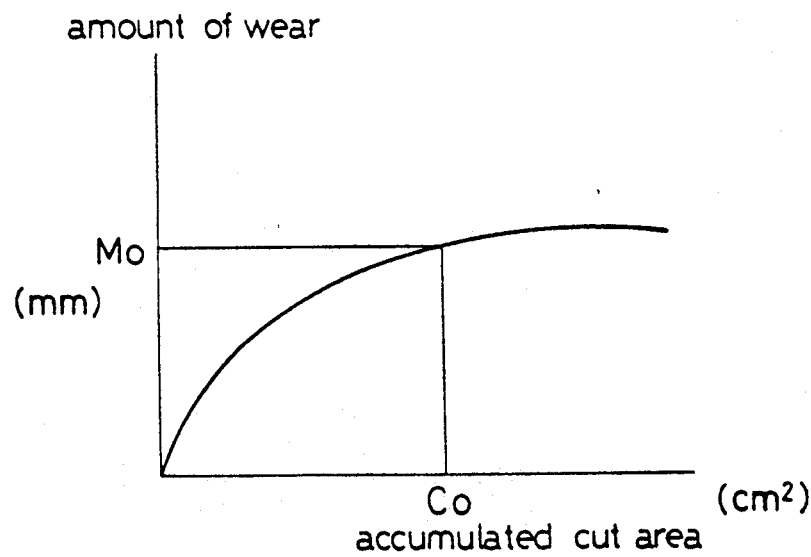
FIG. 10 is an explanatory drawing showing data for the relationship between the amount of wear on the teeth of a sawblade and the accumulated cut surface area, stored in a seventh data base.

As shown in FIG. 10, for each material, dimensions, shape of the workpiece W, and cutting conditions, data for the accumulated cut area related to the amount of wear on the sawblade 7, are filed in the seventh data base 147 as a data base. In FIG. 10, the amount of the accumulated cut area Co corresponding to the wear Mo is the limiting value of the accumulated area. Thus, by comparing the actual accumulated cut area C and the previously set Co a determination of whether the bandsaw blade 7 is being within its life or not can be carried out.

The comparison of the actual detected values of the rearward component force P, the miscut amount K, or the accumulated cut area C with the previously set values Po, Ko, or Co respectively is calculated in the calculation means 123.

Figure 11:
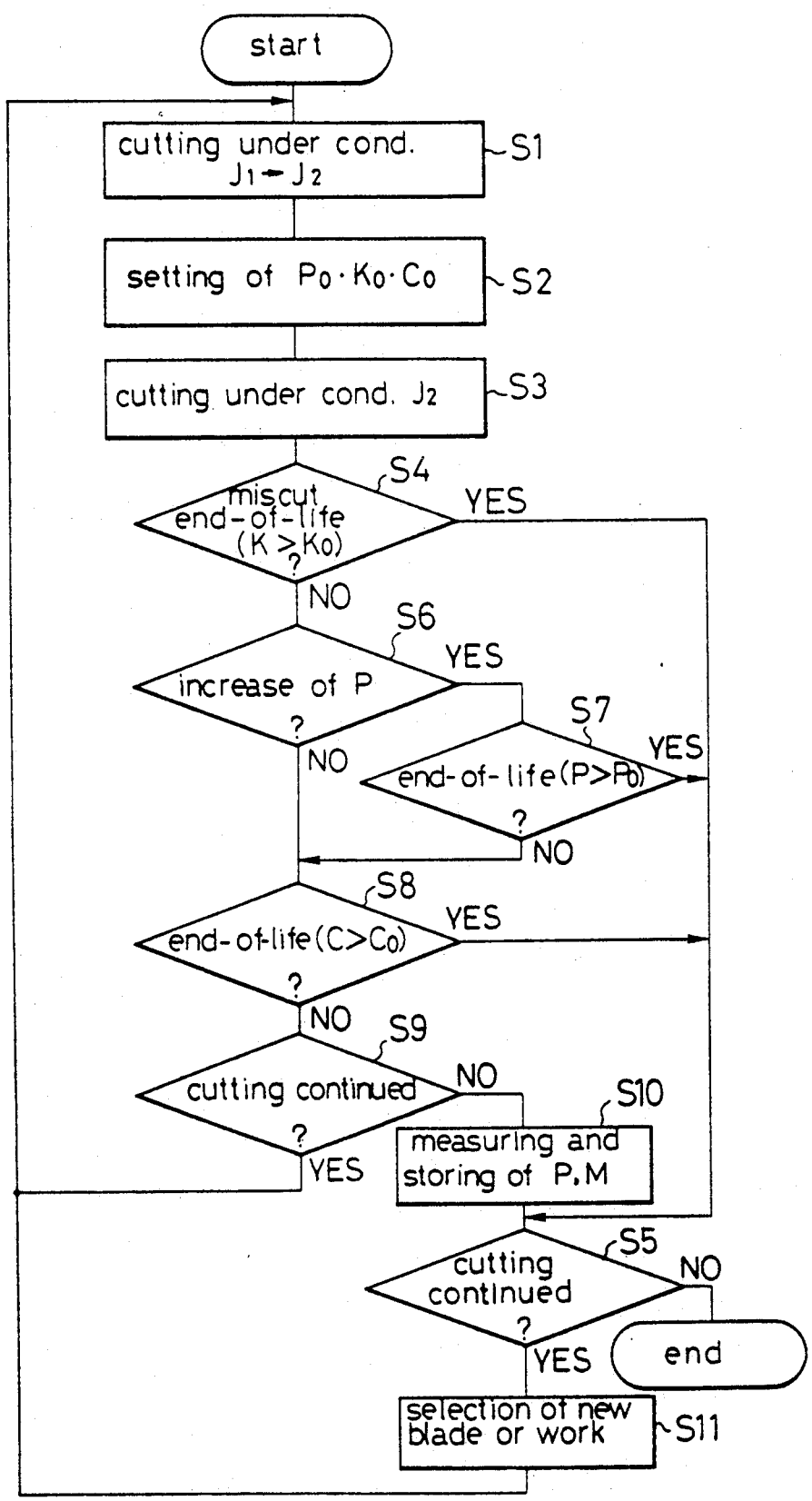
FIG. 11 is a flowchart showing another example of the cutting method.

An explanation of the cutting operation by the sawblade machine having the configuration outlined above will now be given, based on the flowchart of FIG. 11. First, in step S1, the cutting conditions J2 are set for the workpiece W, as previously outlined, from the cutting operation performed on the workpiece W by the sawblade 7, based on the specified cutting conditions J1, which are at a slightly smaller load than the normal cutting conditions.

In step 2, the settings are made for the rearward component force Po, the miscut amount Ko, and the accumulated cut area Co with respect to the limiting amount of wear Mo for the sawblade 7 previously set for the workpiece W, in the graphs shown in FIGS. 8, 9, and 10, filed, in the fifth data base 143, the sixth data base 145, and the seventh data base 147.

In step 3, (after data for cutting the workpiece W under suitable cutting conditions J2 were input from the input device 111), the horizontal bandsaw 1 performs, based on a processing program stored in the process program memory 151, the cutting of the workpiece W under the cutting condition J2 is performed.

During the cutting of the workpiece W under the cutting conditions J2, the determination is made in step S4 as to whether or not a miscut end-of-life could occur. Specifically, a related graph filed in the sixth data base 145 is introduced into the calculation means 123 as shown in FIG. 9, and the actually detected miscut amount K from the miscut detection device 81 is put into use. The actually detected miscut amount K is compared with the miscut amount Ko previously set in the related graph shown in FIG. 9.

If the determination is made that the actually detected miscut amount K is greater than the previously set miscut amount Ko, because the sawblade 7 has reached the end of its life, in step S5 the judgment is made as to whether the cutting process is continued. When it is decided that the cutting process is not continued, the cutting process is terminated. When it is judged that the cutting process is continued, the program proceeds to step S11, and another workpiece W or another sawblade 7 is selected from the menu filed in the menu file 149. The program then returns to the procedures of step S1.

If it is determined in step S4 that the actually detected miscut amount K does not reach the previously set miscut amount Ko, the program proceeds to step S6. In this case, by understanding where the actually detected miscut amount K is located in the graph of FIG. 9 the expected life of the sawblade 7 can be forecast.

In step S6, it is determined whether or not there is an increase in the rearward component force P detected by the rearward component force detection sensor 73. If it is determined that the actually detected rearward component force P has increased more than the already-detected rearward component force, the program proceeds to step S7. It is then determined whether or not the sawblade 7 has reached end of its life, based on the rearward component force P.

Specifically, a graph, as shown in FIG. 8, which is filed in the fifth data base 143 is introduced into the calculation means 123, and, for example, the actually detected rearward component force P from the rearward component force detection sensor 73 is put into use. The actually detected rearward component force P is then compared with the rearward component force Po previously set in the related graph shown in FIG. 8.

If the determination is made that the actually detected rearward component force P is greater than the previously set rearward component force Po, because the sawblade 7 has reached the end of its life, the program proceeds to step S5 and the previously outlined processing is performed.

In step S6, in the case where it is determined that the current actually detected rearward component force P has not increased more than the already-detected rearward component force, or, in step S7 in the case where it is determined that the actually detected rearward component force P has not reached the value of the previously set rearward component force Po, the program proceeds to step S8. In this case, by understanding where the actually detected rearward component force P is located on the curved line in the graph of FIG. 8, it is possible to forecast the life of the sawblade 7.

In step S8 it is determined whether or not the sawblade 7 has reached end of its life, based on the cut area. Specifically, data as shown in FIG. 10, which is filed in the seventh data base 147 are introduced into the calculation means 123, and, for example, by means of the cut area and the number of cuts based on the path of the workpiece W, the actually detected accumulated cut area C is put into use. The actually detected accumulated cut area C is compared with the cut area Co previously set in the related graph shown in FIG. 10.

If the determination is made that the actually detected accumulated cut area C is greater than the previously set cut area Co, because the sawblade 7 has reached the end of its life, the program proceeds to step S5 and the previously outlined processing is performed in step 11. The program then returns to the step S1.

In the case where the determination is made that the actually detected accumulated cut area C has not reached the value of the previously set cut area Co, the program proceeds to step S9. Further, in this case, by understanding where the actually detected accumulated cut area C datum is located on the curved line in graph of FIG. 10, it is possible to forecast the life of the sawblade 7.

In step S9, it is determined whether or not the cut on the workpiece W is continued. Then, if it is judged that the cut is continuously performed on the workpiece W, the program returns to the procedures of step S1, and the process is repeatedly carried out in the manner described above.

If it is judged that the cut on the workpiece W is not continued (e.g. cutting is completed), in step S10 the rearward component force P and the amount of wear A are measured and stored.

In step S5, the decision is made as to whether the cut is continued or not. When it is judged that the cutting process is continued, the program proceeds to step S11, and from the menu filed in the menu file 149, another workpiece W and/or another sawblade 7 is selected and the program returns to step S1.

In this way, while the workpiece W is being cut by the sawblade 7, the actual rearward component force or amount of miscut at a suitable cutting position, or the accumulated cut area are detected, and by comparing this actually detected rearward component force or amount of miscut, or the accumulated cut area with data of the rearward component force, amount of miscut or accumulated cut wear filed in the previously fifth, sixth, and seventh data bases, with the amount of wear on the sawblade 7, it is possible to automatically, accurately and reliably, and easily forecast whether the sawblade 7 has reached its end of life, or at what point it will later reach its end of life. Therefore, the management of the sawblade 7 can be performed better than ever before, to give improved precision and efficiency of the cutting process.

Further, the method of determining the reaching to the end of life of the sawblade 7 is not limited to the embodiment of the present invention just explained. Suitable changes may be made to provide other modes of the present invention.

For example, after performing the cutting process on the workpiece W with the sawblade 7, the surface roughness measuring device 91 provided on the cutting head 9 can contact the end surface of the workpiece W to detect the surface roughness, and by comparing this surface roughness with data of the surface roughness related to the amount of wear of the sawblade 7 filed in a data base, it is possible to automatically, accurately and reliably, and easily determine whether the sawblade 7 has reached its end of life, or at what point it will later reach its end of life.

In addition, by detecting a cutting interval or cutting efficiency instead of accumulated cut area, and by comparing the detected data with data of the cutting interval or cutting efficiency or the like filed in the data base related to the amount of wear on the sawblade 7 or related to the cutting, it is possible to forecast the life expectancy of the sawblade 7.

It is also possible to forecast the end of life of the sawblade 7 by detecting the bending, vibration, noise, and temperature of the sawblade 7 using the bending sensor 83, the vibration sensor 93, the noise sensor 95, and the temperature sensor 97 respectively, and by comparing the measured results with data of bending, vibration, noise, and temperature, versus the amount of wear, or versus the cutting resistance filed in a data base.

By means of the explanation outlined above, while the workpiece is being cut by the sawblade, the actual rearward component force or amount of miscut at a suitable cutting position, or the accumulated cut area and the like is detected, and by comparing this actually detected rearward component force or amount of miscut, or the accumulated cut area and the like with data of the rearward component force, amount, miscut or the accumulated cut area filed in data bases, related to the amount of wear or the cutting resistance, it is possible to automatically, accurately, reliably, and easily determine whether the sawblade has reached its end of life span, or at what point it will later reach its life span. Therefore, the management of the sawblade 7 can be performed better than ever before, to give improved precision and efficiency of the cutting process.

What is claimed is:

1. A workability detection method for cutting a workpiece, comprising the steps of:
   cutting a workpiece up to a certain position as a result of which the load on a blade of the cutting machine is kept relatively small;
   detecting the cutting resistance during the cutting operation;

comparing the detected data with back-up data which has been previously obtained and stored in a data base of a data storing means for the workpiece cut by the same type of blade; and judging workability of cutting by determining whether the detected data is within a predetermined range of values stored in the database.

2. The cutting method of claim 1, further comprising repeating the steps of detecting the data, and comparing the detected data with corresponding data which is stored in a data base and then judging workability of cutting.

3. A workability detection method for cutting a workpiece, comprising the steps of:

cutting a workpiece up to a certain position as a result of which the load on a blade of the cutting machine is kept relatively small;

detecting the cutting time to cut to a specified position of the workpiece;

comparing the detected data with back-up data which has been previously obtained and stored in a data base of a data storing means for the workpiece cut by the same type of blade; and judging workability of cutting by determining whether the detected data is within a predetermined range of values stored in the database.

4. The cutting method of claim 3, further comprising repeating the steps of detecting the data, and comparing the detected data with corresponding data which is stored in a data base and then judging workability of cutting.

5. A workability detection method for cutting a workpiece, comprising the steps of:

cutting a workpiece up to a certain position as a result of which the load on a blade of the cutting machine is kept relatively small;

detecting the amount of the wear on said blade to cut to a specified position of the workpiece;

comparing the detected data with back-up data which has been previously obtained and stored in a data base of a data storing means for the workpiece cut by the same type of blade; and judging workability of cutting by determining whether the detected data is within a predetermined range of values stored in the database.

6. The cutting method of claim 5 further comprising the steps of:

repeating the step of selecting an appropriate cutting condition by judging the workability of cutting of the workpiece when continuous cutting is possible, and proceeding in cutting the workpiece further up to a next predetermined position.

7. The cutting method of claim 5, wherein the judging of workability of cutting the workpiece is made by detecting at least one of the cutting resistance during the cutting to a certain position, the cutting time during the cutting to the certain position, the amount of the wear of the blade during the cutting to the certain position and the amount of the cut during a certain period of time, and comparing said detected data with data previously stored in a data storing means.

8. The cutting method of claim 5, further comprising repeating the steps of detecting the data, and comparing the detected data with corresponding data which is stored in a data base and then judging workability of cutting.

9. A workability detection method for cutting a workpiece, comprising the steps of:

cutting a workpiece up to a certain position as a result of which the load on a blade of the cutting machine is kept relatively small;

detecting the feeding position of the blade on the workpiece after a specified cutting time;

comparing the detected data with back-up data which has been previously obtained and stored in a data base of a data storing means for the workpiece cut by the same type of blade; and judging workability of cutting by determining whether the detected data is within a predetermined range of values stored in the database.

10. The cutting method of claim 9, wherein the judging of workability of cutting the workpiece is made by detecting at least one of the cutting resistance during the cutting to a certain position, the cutting time during the cutting to the certain position, the amount of the wear of the blade during the cutting to the certain position and the amount of the cut during a certain period of time, and comparing said detected data with data previously stored in a data storing means.

11. The cutting method of claim 7, further comprising repeating the steps of detecting the data, and comparing the detected data with corresponding data which is stored in a data base and then judging workability of cutting.

12. A workability detection method for cutting a workpiece, comprising the steps of:

cutting a workpiece up to a certain position as a result which the load on a blade of the cutting machine is kept relatively small;

detecting the amount of processing of the workpiece, such as a cross-sectional area cut and a length along which the workpiece is processed after a specified cutting time;

comparing the detected data with back-up data which has been previously obtained and stored in a data base of a data storing means for the workpiece cut by the same type of blade; and judging workability of cutting by determining whether the detected data is within a predetermined range of values stored in the database.

13. The cutting method of claim 12, further comprising repeating the steps of detecting the data, and comparing the detected data with corresponding data which is stored in a data base and then judging workability of cutting.

14. A cutting method by means of a cutting machine as a result of which the load on a blade of the cutting machine is kept relatively small;

detecting one of:

the cutting resistance at a predetermined feeding position of the blade on the workpiece;

the cutting time interval when a cut is made up to a predetermined specified position on the workpiece;

the amount of the wear of the blade when a cut is made to a predetermined specified position on the workpiece;

the feeding position of the blade on a workpiece after a specified cutting time; and the amount of processing by the blade, such as a cross-sectional area cut and a length along with the workpiece is processed after a specified cutting time;

comparing the detected data with back-up data which has been previously obtained and stored in a data base of a data storing means for the workpiece cut by the same type of blade;

judging workability of cutting by determining whether the detected data is within a predetermined range of values stored in the database;

determining suitable cutting conditions based on the result of the judgment of the workability; and performing a cutting process on the workpiece based on the determined cutting conditions.

15. The cutting method of claim 14, further comprising repeating the steps of detecting the data, and comparing the detected data with corresponding data which is stored in a data base and then judging workability of cutting.

16. A workability detection device for a workpiece comprising:

means for cutting a workpiece to a certain position as a result of which the load on a blade of the cutting machine is kept relatively small;

means for detecting at least one of the cutting resistance during the cutting operation, the cutting time to make a cut to a specified position of the workpiece, the amount of the wear of the blade of the cutting means to cut to a specified position of the workpiece, the feeding position of the blade on the workpiece after a specified cutting time, and the amount of processing on the workpiece such as a cross-sectional area cut and a length along which the workpiece is processed after a specified cutting time; and means for comparing the detected data with back-up data which has been previously obtained and stored in a data base for the workpiece cut by the same type of blade.

17. A cutting method by means of a cutting machine on a workpiece comprising the steps of:

cutting a workpiece to a certain position as a result of which the load on a blade of the cutting machine is kept relatively small;

detecting a miscut amount of the workpiece by a miscut detection means during said cutting;

comparing, when the blade reaches the said position, said detected miscut amount with a miscut limiting value previously obtained and stored in a data base for the workpiece cut by the same type of blade and determining whether or not the blade has reached a miscut end-of-life;

selecting an appropriate cutting condition by judging the workability of cutting of the workpiece when continuous cutting is possible, and proceeding in cutting the workpiece further up to a next certain position, and replacing the blade at its end-of-life with a new one when the blade reaches its miscut end-of-life during the above steps.

18. A cutting machine for a workpiece comprising:

means for cutting a workpiece as a result of which the load on a blade of the cutting machine is kept relatively small;

means for detecting at least one of the cutting resistance during the cutting operation, the cutting time to make a cut to a specified position of the workpiece, the amount of the wear of the blade of the cutting means to cut to a specified position of the workpiece, the feeding position of the blade on the workpiece after a specified cutting time, and the amount of processing on the workpiece such as a cross-sectional area cut and a length along which the workpiece is processes after a specified cutting time; and means for comparing the detected data with back-up data which has been previously obtained and stored in a data base for the workpiece cut by the same type of blade.

* * * * *

UNITED STATES PATENT AND TRADEMARK OFFICE
CERTIFICATE OF CORRECTION

PATENT NO. : 5,115,403
DATED : May 19, 1992
INVENTOR(S) : Akiyoshi Yoneda, et. al.

It is certified that error appears in the above-indentified patent and that said Letters Patent is hereby corrected as shown below:

Column 2, line 24, delete "is"--.

Claim 11, column 18, line 22, "claim 7" should be --claim 9--.

Claim 14, column 18, line 64 "with" should be --which--.

Claim 18 should read as follows:

--A cutting machine for a workpiece comprising:

means for cutting a workpiece as a result of which the load on a blade of the cutting machine is kept relatively small;

means for detecting a miscut amount of the workpiece;

means for storing data; and means for comparing said detected data with data previously stored in said data storing means.--

Signed and Sealed this

Seventeenth Day of August, 1993

Attest:

BRUCE LEHMAN

*Attesting Officer*　　　*Commissioner of Patents and Trademarks*